United States Patent [19]

Laruelle et al.

[11] Patent Number: 4,764,518
[45] Date of Patent: Aug. 16, 1988

[54] ANTIBACTERIAL AGENTS CONTAINING OXO-4-PYRIDINE CARBOXYLIC ACID DERIVATIVES

[75] Inventors: Claude Laruelle, Villeneuve-Loubet; Marcel Lepant, Nice; Bernard Raynier, Cagnes, all of France

[73] Assignee: Panmedica, Carros, France

[21] Appl. No.: 874,232

[22] Filed: Jun. 13, 1986

[30] Foreign Application Priority Data

Jun. 20, 1985 [FR] France ............... 85 09371

[51] Int. Cl.⁴ ............... A61K 31/335; A61K 31/47;
A61K 31/50; A61K 31/505; C07D 491/056;
C07D 491/147; C07D 239/00; C07D 237/00
[52] U.S. Cl. ........................... 514/291; 546/83;
546/90; 546/156; 546/123; 544/234; 544/235;
544/250; 544/279; 544/345; 544/350; 514/248;
514/249; 514/267; 514/293; 514/300; 514/312
[58] Field of Search ............ 546/15, 18, 83, 90,
546/156, 123; 544/279, 350, 234, 235, 250, 345;
514/300, 312, 259, 248, 249, 267, 291, 293

[56] References Cited

U.S. PATENT DOCUMENTS 3,590,036   6/1971   Lesher et al. ............ 546/156
4,036,962   7/1977   Lee ......................... 546/90

Primary Examiner—Mary C. Lee
Assistant Examiner—J. Richter
Attorney, Agent, or Firm—Bell, Seltzer, Park & Gibson

[57] ABSTRACT

The present invention relates to novel antibacterial agents, corresponding to the following general formula I

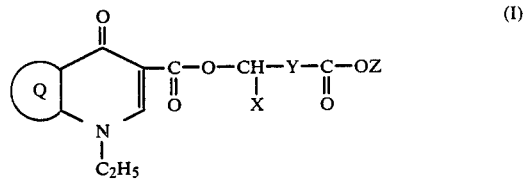

in which:
Q represents an aromatic ring,
X represents a hydrogen atom or a linear or branched alkyl group,
Y represents a linkage or an alkyl group,
Z represents a hydrogen atom, an alkyl, aralkyl or heteroalkyl group, These compounds constitute anti-bacterial agents with multiple pharmacological activity.

9 Claims, No Drawings

ANTIBACTERIAL AGENTS CONTAINING OXO-4-PYRIDINE CARBOXYLIC ACID DERIVATIVES

BACKGROUND OF THE INVENTION

The present invention relates to novel antibacterial agents with multiple pharmacological action and to their process of preparation.

Research for antibacterial agents has led to the discovery of a wide variety of structures related to 1,4-dihydro 1-alkyl 4-oxo pyridine 3-carboxylic acids.

Thus, DAINIPPON pharmaceutical in British Pat. No. 1,129,358 (1966) describes the interesting antibacterial properties of derivatives of the general formula:

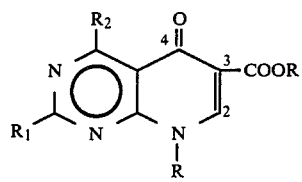

comprising among others PIROMIDIC acid when $R_1$=pyrrolidine.

The same applicant describes, in its French Pat. No. 2,103,618 (1971) much superior antibacterial properties when the previously mentioned pyrrolidine ring is substituted. From the same basic structure, DAINIPPON claims in its French Pat. No. 2,196,159 (1973) the general structure:

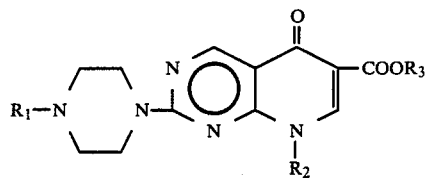

whose bactericidal activities are more interesting than those of the previously described homologs. Somewhat later, R. BELLON in his French Pat. No. 2,364,920 (1977) claims derivatives according to the above general formula giving the radical $R_1$, meanings not previously claimed, namely carbonyl radicals, whereas at the same time DAINIPPON in its French Pat. No. 2,359,140 (1977) claimed this same general formula but where $R_1$=$NH_2$—phényl—$CH_2$— resulting in an antibacterial activity which was quite satisfactory both in vitro and in vivo against gram positive and gram negative bacteria.

In this same series of 1-alkyl 4-pyridone 3-carboxylic acids, NALIDIXIC acid was the subject of French application No. 1,427,608 (1962) of STERLING DRUG according to the general formula:

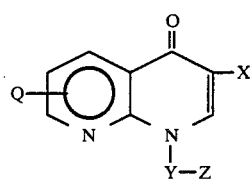

where X represents a carboxy, carbalkoxy, or carbamyl group.

From this structure, YAMANOUCHI formed the amide of ampicillin (B. Fr. 2,183,895) and FUJIMOTO that of cephalexine (B. Jap. 82.46990).

This general structure is defined by R. BELLON B. Fr. No. 2,500,833 who claims the derivatives of the general formula:

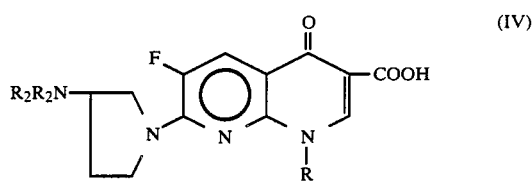

for its bactericidal activities particularly with respect to grams.

The series of 1,4 dihydro 1-ethyl 4-oxo pyridine carboxylic acids determines with a condensed aromatic ring a quinolone of which oxolinic acid:

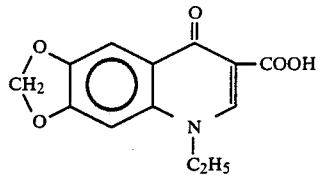

represents the head of the series (B. Fr. M 4148 WARNER LAMBERT). This 3 carboxylic quinolone structure was gradually refined to arrive at PERFLOXACINE.

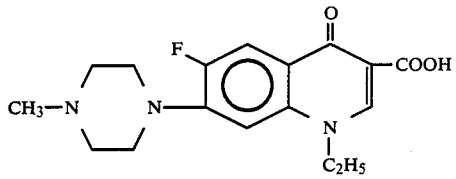

of Roger BELLON, or at ROSOXACINE of STERLING DRUG (U.S. Pat. No. 3.753.993),

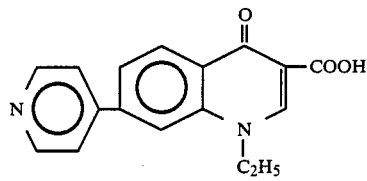

or again NORFLOXACINE (U.S. Pat. No. 4,292,317).

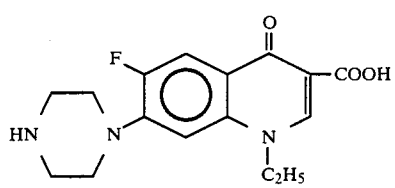

It is seen that therefore in the course of time structures have been evolved with the same basic structure and whose pharmacological properties particularly antibacterial are increasing.

The derivatives of oxolinic or nalidixic acid, ENOXACINE, PERFLOXACINE, NORFLOXACINE, ROSOXACINE or the derivatives of pipemidic acid are very valued and widely used antibacterial agents.

GENERAL DESCRIPTION

It is an object of the present invention to provide a novel family of antibacterial agents encompassing derivatives of the above-named products and a good many others also.

It is also an object of the invention to widen the antibacterial spectrum of these products and to add other pharmacological actions to their antibacterial activity.

According to the present invention there are provided compounds corresponding to the following general formula (I):

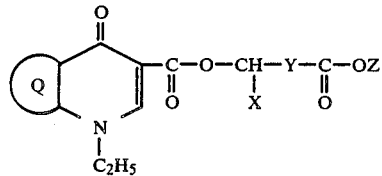

in which, Q represents an aromatic ring possibly substituted or a heterocyclic ring comprising one or two nitrogen atoms, possibly substituted, X represents a hydrogen atom or a linear alkyl group comprising 1 to 6 carbon atoms or a phenyl nucleus possibly substituted, Y represents a linear or branched alkyl group, comprising from 1 to 10 carbon atoms and Z represents a hydrogen atom,
  or a linear or branched alkyl group, containing 1 to 11 carbon atoms, and which can determine a saturated ring constituted by 4 to 7 carbon atoms,
  or an aralkyl group, comprising 7 to 12 carbon atoms,
  or an aliphatic chain of 1 to 4 methylene groups, linked to a heterocyclic ring with 5 or 6 links, the heteroatom being selected from among nitrogen, oxygen, and sulfur
  or a heteroalkyl group, comprising from 1 to 10 carbon atoms, the heteroatom being selected from among nitrogen, oxygen, and sulfur.

The derivatives according to the invention are remarkable antibacterial agents with a wide spectrum possessing diuretic activity and they show in addition interesting bronchodilator activities. They antagonize histamine, acetylcholine and serotonin and show themselves to be antidepressant agents in vivo.

The significance of the aromatic ring Q is applied, for example, to a derivative of oxolinic acid where Q is methylenedioxy-phenyl or indeed nalidixic acid, Q determining with the carboxylic pyridone group a 1-ethyl 4-oxo 1,4-dihydro 7-methyl 3-naphtyridinyl unit.

When Q represents a 2-piperazinyl 3-fluoro 5-6 condensed pyridine, the aromatic unit represents ENOXACINE. When Q represents a 5-6 condensed 2-piperazinyl pyridine, the unit of PIPEMIDIC acid is then obtained.

When Q represents a phenyl ring, the latter may be substituted to form 1-ethyl 4-oxo 6-fluoro 7-[4-methyl]1-piperazinyl 1,4-dihydro 3-quinoline carboxylic acid or PEFLOXACINE.

If the 7 substituent is an unsubstituted piperazine the aromatic unit describes NORFLOXACINE.

If Q represents a phenyl ring and is substituted by a pyridinyl radical, the aromatic group then represents ROSOXACINE or 1-ethyl 4-oxo 7-(4-pyridyl)1,4-dihydro 3-quinoline carboxylic acid.

According to another aspect of the invention there is provided a process for the preparation of the compounds corresponding to the general formula (I).

This process comprises the alkylation of an alkli or alkaline earth salt of an acid of the general formula (II),

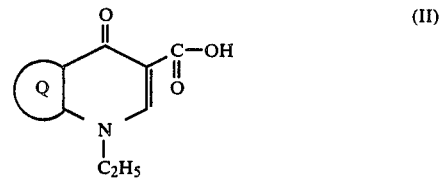

in which Q has the same meaning as above. The alkylating agent is selected from among the alkyl halogenides corresponding to the general formula (III),

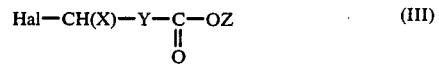

in which Hal represents a chlorine or bromine atom, more advantageously a bromine atom and X, Y, Z have the previously defined meanings.

The compounds corresponding to formula (III) are prepared by alkylation of an alcohol Z—OH, Z being different from hydrogen or from a tert-butyl group, through the bromide of monobromoacetic acid or the chloride of monochloroacetic acid. The acylation is performed in an inert solvent, such as haloalkanes, ethers, ketones, alone or mixed, more specifically selected from among chloroform, methylene chloride, diethyl ether, tetrahydrofuran, acetone. The reaction is generally conducted in the presence of an acid acceptor, more exactly pyridine or triethylamine, at a temperature comprised between 20° and 110°, more generally at ambient temperature.

The compounds corresponding to the general formula (III), in which Z is a t. butyl group, are prepared by a known technique (Bull. Soc. Chim. Fr., (1974), 12, 2985-6), in acid catalysis by concentrated sulfuric acid, in the presence of t. butyl alcohol, at ordinary temperature.

The reaction leading to the compounds of general formula (I), between the alkali or alkaline earth salt of the compound of general formula (II) and the compound of general formula (III), is carried out at a temperature comprised of between 20° and 100°, more advantageously at ordinary temperature, in an inert solvent. The solvent is selected among dimethylsulfoxide, hexamethylphosphoretriamide, or amides such as N,N dimethylformamide or N,N dimethylacetamide, mostly N,N dimethylformamide. The compounds of general formula (I), with Q, X and Y having the same meaning as previously and where Z represents a hydrogen atom, are easily obtained by acid hydrolysis, more advantageously with trifluoacetic acid, of a derivative of the general formula (I), where Z represents a t. butyl group.

The hydrolysis is carried out at a temperature comprised between 0° and 30°. When Z represents a benzyl group, they may also be obtained by hydrogenolysis in the presence of palladium on carbon.

DESCRIPTION OF PREFERRED EMBODIMENTS

The invention will be better understood by means of the additional description which follows, which refers to examples of preparation of products according to the invention, as well as to an account of the experiments relating to the pharmacological activity of products according to the invention. It must be well understood, however, that these examples and reports are given purely by way of illustration of the invention, of which they do not constitute in any way a limitation thereof.

All the products obtained were subjected to thin layer chromatography and show only a single spot. The thin layer chromatographs (TLC) were done on a Kieselgel F 254 plate and developed, in the following systems:

A: Toluene 10; ethyl formal 10; formic acid 1
B: chloroform 30; methanol 2
C: n. butanol 8; acetic acid 1; water 1 and revealed by ultra-violet light at 254 nm. Centesimal analyses carried out on all the products accord with those calculated from the theoretical formulae.

EXAMPLE I

Ethyl [1-Ethyl 4-Oxo 1,4-Dihydro 7-Methyl 3-Naphtyridinyl]4-Carbonyloxy, Butyrate To a suspension of 17.8 g (70 mM) of the sodium salt of [1-ethyl 4-oxo 1,4-dihydro 7-methyl 3-naphtyridinyl]-carboxylic acid, in 450 ml in dimethylformamide, is added in 15 minutes, at ordinary temperature, a solution of 13.85 g (71 mM) of ethyl 4-bromo butyrate in 50 ml of dimethylformamide. Stirring is kept up for 48 hours at ordinary temperature, and the solvent removed under reduced pressure.

The residue is taken up with 150 ml of 0.2N iced sodium hydroxide, extracted with chloroform, then the chloroform layer is washed with 0.5N sodium hydroxide, with water, and dried over sodium sulfate. After evaporation of the chloroform; the residue is triturated with ethyl ether, then taken up again in petroleum ether in the cold. It is filtered, dried and 47% of a pure product obtained, Rf=0.23 (A), Rf=0.86 (B), m.p.=89°–90°

NMR spectrum, in solution in CDCl$_3$, relative to TMS: 9.05 ppm, (s), N—CH=, 1H; 7.25 and 8.60 ppm, (m), H arom, 2H; 4.45 ppm, (q), NCH$_2$CH$_3$, 3H; 4.15 ppm (m) COOCH$_2$—, 4H; 2.70 ppm, (s), C(CH$_3$)—N, 3H; 2.25 and 2.60 ppm, (m), —CH$_2$—CH$_2$—CH$_2$COO—, 4H; 1.30 and 1.55 ppm, (2t) N—CH$_2$CH$_3$ and COOCH$_2$—CH$_3$, 6H.

EXAMPLE II

[Ethyl 1-Ethyl 4-Oxo 6,7-Methylenedioxy 3-Quinolinyl]4-Carbonyloxy Butyrate

To a suspension of 19.8 g (70 mM) of the sodium salt of [1-ethyl 4-oxo 6,7-methylenedioxy 1,4-dihydro 3-quinolinyl]carboxylic acid in 450 ml of dimthylformamide, is added, in 15 minutes, at ambient temperature, a solution of 13.85 g (71 mM) of ethyl 4-bromo butyrate in 50 ml of dimethylformamide. Stirring is kept up for 48 hours at ordinary temperature and the solvent removed under reduced pressure. The residue from evaporation is taken up again in 150 ml of 0.2N acid caustic soda, it is extracted with chloroform, washed with 0.5N caustic soda, with water, and dried on sodium sulfate. The chloroform is evaporated, the residue taken up again with ethyl ether, evaporated and taken up again with petroleum ether, at ordinary temperature, filtered, dried and 48% of a pure product obtained, Rf=0.08 (A), Rf=0.62 (B), Rf=0.48 (C), m.p.=105°–7°.

NMR spectrum, in solution in CDCl$_3$, relative to TMS: 8.30 ppm, (S), N—CH=C, 1H; 6.85 and 7.35 ppm, (2s), aromatic H at ortho position to the methylene dioxy, 2H; 6.10 ppm (s), O—CH$_2$—O; 2H; 4.35 ppm, (m), COO—CH$_2$; 4.15 ppm, (q), N—CH$_2$CH$_3$, 2H; 2.10 and 2.50 ppm, (q and t), —COOCH$_2$CH$_2$CH$_2$COO—, 4H; 1.25 and 1.50 ppm, (2t), NCH$_2$CH$_3$ and COOCH$_2$CH$_3$, 6H.

EXAMPLE III

[Ethyl 1-Ethyl 4-Oxo 1,4-Dihydro 7-Methyl 3-Naphthyridinyl]2-Carbonyloxy Butyrate 13.85 g (71 mM) of ethyl 2-bromo butyrate is added to a suspension of 17.8 g (70 mM) of the sodium salt of [1-ethyl 4-oxo 1,4-dihydro 7-methyl 3-naphtyridinyl]-carboxylic acid, in 500 ml of dimethylformamide. Stirring is kept up for 48 hours, at an ambient temperature, and then evaporated to dryness. The residue is taken up again with 150 ml iced 0.2N caustic soda, then extracted with chloroform. The chloroform layer is washed with 0.5N caustic soda, with water, then dried over sodium sulfate. After evaporation, the residue is triturated in ethyl ether, the ether is evaporated, the residue made into a paste in petroleum ether. After filtration and drying, 69% of a pure product are obtained; Rf=0.40 (A); RF=0.82 (B); Rf=0.78 (C); m.p.=118°–9°.

NMR spectrum, in solution in CDCl$_3$, relative to TMS: 9.05 ppm; (S), N—CH=, 1H; 7.25 and 8.60 ppm, (m), H arom, 2H; 5.15 ppm, (t), COOCH(CH$_3$)COO, 1H; 4.40 ppm, (q), NCH$_2$CH$_3$, 2H; 4.20 ppm, (q), COOCH$_2$CH$_3$, 2H; 2.65 ppm (s), C(CH$_3$)—N, 3H; 2.05 ppm, (m), —CH—CH$_2$CH$_3$, 2H; 1.15 to 1.60 ppm, (m) —CH$_2$—CH$_3$, 9H.

EXAMPLE IV

[Ethyl 1-Ethyl 4-Oxo 6,7-Methylenedioxy 1,4-Dihydro 3-Quinolinyl]2-Carbonyloxy Butyrate 15.8 G (81 mM) of ethyl 2-bromo butyrate are added to a suspension of 22.65 g (80 mM) of the sodium salt of [1-ethyl 4-oxo 1,4-dihydro 7-methyl 3 quinolinyl carboxylic acid in 550 ml of dimethylformamide. Stirring is maintained at ordinary temperature, for 48 hours, then evaporated to dryness. The residue is taken up in 150 ml of 0.2N iced caustic sode, extracted with chloroform, washed with 0.5 n caustic soda, then with water, it is then dried over sodium sulfate, and evaporated. The residue is made into a paste in petroleum ether, in the cold, filtered, dried. In this way 45% of a pure product are obtained; Rf=0.10 (A); Rf=0.63 (B); Rf=0.67 (C); m.p.=161°–3°.

NMR spectrum, in solution in CDCl$_3$, relative to TMS: 8.35 ppm, (s), NCH=C—, 1H; 6.85 and 7.70 ppm, (2s), H arom, 2H; 6.10 ppm, (s), O—CH$_2$—O, 2H; 5.15 ppm, (t), COOCH—, 1H; 4.20 ppm, (m), N—CH$_2$ and COOCH$_2$—, 4H; 2.0 ppm, (m), —CH—CH$_2$CH$_3$, 2H; 1.05 to 1.50 ppm, (m), —CH$_2$—CH$_3$, 9H.

EXAMPLE V

Ethyl[1-Ethyl 4-Oxo 1,4-Dihydro 7-Methyl 3-Naphtyridinyl]5-Carbonyloxy Valerate 11.7 g (56 mM) of ethyl 5-bromo valerate are added to a suspension of 14 g (55 mM) of the sodium salt of [1-ethyl 4-oxo 1,4 dihydro 7-methyl 3-naphtyridinyl]-carboxylic acid, in 400 ml of dimethylformamide. It is stirred at ordinary temperature for 48 hours and then evaporated to dryness. The residue is taken up again in 120 ml of iced 0.2N caustic soda, and extracted with chloroform. The chloroform layer is washed with 0.5N caustic soda, with water, it is dried and evaporated. The pasty residue is made into a paste in petroleum ether, in the cold. It is filtered, dried and 25% of a pure product is obtained, Rf=0.78 (B), Rf=0.75 (C), m.p.=114°-5°.

NMR spectrum, in solution in $CDCl_3$, relative to TMS: 9.10 ppm, (s), N—CH=, 1H; 7.25 and 8.60 ppm, (m), H arom, 2H; 4.10 to 4.55 ppm, (m), $NCH_2CH_3$, $2COOCH_2$, 6H; 2.65 ppm, (s)=C($CH_3$)—N, 3H; 2.40 ppm, (t), $CH_2COO$—, 2H; 1.85 ppm, (m), —$CH_2CH_2$—, 4H; 1.30 to 1.55 ppm; (2t); $NCH_2CH_3$ and $COOCH_2CH_3$, 6H.

EXAMPLE VI

Ethyl[1-Ethyl 4-Oxo 6,7-Methylenedioxy 1,4-Dihydro 3-Quinolinyl]5-Carbonyloxy Valerate 11.7 g (56 mM) of ethyl 5-bromo valerate, is added to a suspension of 15.6 g (55 mM), of the sodium salt of [1-ethyl 4-oxo 6,7-methylenedioxy 1,4-dihydro 3-quinolinyl]carboxylic acid in 370 ml of dimethylformamide. It is stirred at ordinary temperature for 48 hours, evaporated to dryness. The residue is taken up again in 120 ml of 0.2 iced caustic soda, extracted with chloroform. The chloroform layer is washed with 0.5N caustic soda, with water, dried and evaporated. The oily residue is covered with petroleum ether for 15 hours. It is filtered, dried and 33% of a pure product is obtained, Rf=0.57 (B); Rf=0.56 (C), m.p.=139°-40°.

NMR spectrum, in solution in $CDCl_3$, relative to TMS: 8.30 ppm, (s), N—CH=, 1H; 6.85 and 7.80 ppm, (2s), H arom, 2H; 6.10 ppm, (s), $OCH_2O$, 2H; 4.10 and 4.20 ppm, (m), N—$CH_2$ and $COOCH_2$—, 4H; 2.40 ppm; (t), $CH_2COO$, 2H; 1.80 ppm, (m), —$CH_2$—$CH_2$—, 4H; 1.20 to 1.55 ppm, (2t), N—$CH_2CH_3$ and $COOCH_2CH_3$, 6H.

EXAMPLE VII n-Heptyl[1-Ethyl 4-Oxo 1,4-Dihydro 7-Methyl 3-Naphtyridinyl]Carbonyloxyacetate (1) Heptyl bromoacetate:

101 g (0.5M) of bromide of bromoacetic acid is run into a solution of 58 g (0.5M) of heptanol, 50.7 g (0.5M) of triethylamine, in 600 ml of anhydrous ether, kept at 10°. It is stirred at ordinary temperature for 15 hours, filtered, the ether layer washed with water, dried and distilled. 56% of a pure product is obtained, b.p.=85° (0.25 mm).

(2) 11.9 g (50 mM) of n-heptyl bromoacetate is added to a suspension of 13.2 g (52 mM) of the sodium salt of [1-ethyl 4-oxo 1,4-dihydro 7-methyl 3naphtyridinyl]carboxylic acid, in 400 ml of dimethylformamide. It is stirred at ordinary temperature for 48 hours, evaporated to dryness, and the residue taken up again in 120 ml of iced 0.2N caustic soda. It is exstracted with chloroform, washed with 0.5N caustic soda, with water, dried and evaporated. The oily residue is covered with petroleum ether and left at ordinary temperature for 15 hours. It is filtered and 90% of a pure product is obtained, Rf=0.46 (A); Rf=0.85 (B); m.p.=59°.

NMR spectrum in solution in $CDCl_3$ with respect to TMS: 8.75 ppm, (s), N+$CH$—, 1H; 7.20 and 8.55 ppm (m), H arom, 2H; 4.85 ppm, (s), —$COOCH_2COO$—, 2H; 4.10 to 4.60 ppm, (q) and (t) N—$CH_2$— and $COOCH_2CH_2$, 4H; 2.65 ppm, (s), —C($CH_3$)—N, 3H; 1.20 to 1.70 ppm, (m), —($CH_2$)$_5$—, N—$CH_2CH_3$, 13H; 0.85 ppm, (t), —($CH_2$)$_6CH_3$, 3H

EXAMPLE VIII n-Heptyl[1-Ethyl 4-Oxo 6,7-Methylenedioxy 1,4-Dihydro 3-Quinolinyl]Carbonyloxy Acetate 11.9 g (50 mM) of heptyl bromoacetate, prepared according to the technique previously explained (ex VII-1), is added to a suspension of 14.7 g (52 mM) of the sodium salt of [1-ethyl 4-oxo 6,7-methylenedioxy 1,4-dihydro 3-quinolinyl]carboxylic acid, in 400 ml of dimethylformamide. It is shaken at ordinary temperature for 48 hours, solution obtained evaporated, and the residue is taken up again in iced 0.2N caustic soda; it is extracted with chloroform and washed with 0.5N caustic soda, with water, dried and evaporated. The oily residue is taken up again in 200 ml of petroleum ether, left at ordinary temperature for 15 hours. It is filtered and 92% of a pure product obtained, Rf=0.13 (A); Rf=0.67 (B); m.p.=97°-8°.

NMR spectrum in solution in $CDCl_3$, with respect to TMS: 8.40 ppm, (s); N—CH=, 1H; 6.85 and 7.70 ppm, (2s), H arom, 2H; 6.05 ppm, (s), —O—$CH_2$—O—, 2H; 4.85 ppm, (s), $COOCH_2COO$—, 2H; 4.15 ppm, (m), N—$CH_2$— and COO—$CH_2$—, 4H; 1.20 to 1.70 ppm, N—$CH_2CH_3$, —($CH_2$)$_5$—, 13H; 0.90 ppm, (t), —($CH_2$)$_6CH_3$, 3H.

EXAMPLE IX n-Nonyl[1-Ethyl 4-Oxo 1,4-Dihydro 7-Methyl 3-Naphthyridinyl]Carbonyloxyacetate (1) Nonyl bromoacetate:

101 g (0.5M) of bromoacetic acid bromide is run on to a solution of 72 g (0.5M) of nonanol, 50.7 g (0.5M) of triethylamine, in 600 ml of anhydrous ethyl ether, kept at 10°. It is stirred at ordinary temperature for 15 hours, filtered, the solvent is evaporated and it is distilled under reduced pressure. 52% of a pure product is obtained, b.p.=95° (0.25 mm).

(2) 13.25 g (50 mM) of nonyl bromoacetate is added to a suspension of 13.2 g (52 mM) of the sodium salt of [1-ethyl, 1,4-dihydro 7-methyl 4-oxo 3-naphtyridinyl]-carboxylic acid, in 400 ml of dimethylformamide. It is stirred at ordinary temperature for 48 hours, and the solution obtained evaporated to dryness. The residue is taken up again in 150 ml of 0.2N iced caustic soda, and extracted with chloroform. The chloroform layer is washed with 0.5N caustic soda, with water, dried and evaporated. The oily residue is covered with petroleum ether for 15 hours. It is filtered and 85% of a pure product obtained, Rf=0.54 (A); Rf=0.86 (B); m.p.=56°-7°.

NMR spectrum, in solution in $CDCl_3$, with respect to TMS: 8.70 ppm, (s), N=CH—, 1H; 7.20 and 8.60 ppm, (m), H arom, 2H; 4.85 ppm, (s), —$COOCH_2COO$—, 2H; 4.10 to 4.65 ppm, (q) and (t), N—$CH_2$—$CH_3$ and $COOCH_2CH_2$, 4H; 2.56 ppm, (s), —C($CH_3$)—N, 3H; 1.20 to 1.70 ppm, (m), —($CH_2$)$_7CH_3$ and N—$CH_2CH_3$, 17H; 0.85 ppm, (t), ($CH_2$)$_7CH_3$, 3H.

EXAMPLE X n-Nonyl[1-Ethyl 4-Oxo 6,7-Methylenedioxy 1,4 Dihydro 3-Quinolinyl]Carbonyloxyacetate 13.25 g (50 mM) of n-nonyl bromoacetate, prepared according to the technique explained in example IX-1, is added to a suspension of 14.7 g (52 mM) of the sodium salt of [1-ethyl 4-oxo 6,7-methylenedioxy 1,4-dihydro 3-quinolinyl]carboxylic acid in 400 ml of dimethylformamide. It is stirred at ordinary temperature for 48 hours, and the solution obtained evaporated to dryness. The residue is taken up in 150 ml of 0.2N iced caustic soda, extracted with chloroform. The chloroform layer is washed with 0.5N caustic soda, with water, it is dried and evaporated. The oily residue is covered with petroleum ether for 2 hours, then filtered. 88% of a pure product is obtained, Rf=0.15 (A); Rf=0.68 (B); m.p.=82°.

NMR spectrum, in solution in $CDCl_3$, with respect to TMS: 8.35 ppm, (s), N—CH=, 1H; 6.85 and 7.70 ppm, (2s), H arom, 2H; 6.10 ppm, (s) —O—CH$_2$—O—, 2H; 4.85 ppm, (s), COO—CH$_2$—COO, 2H; 4.05 to 4.30 ppm, (m), N—CH$_2$CH$_3$ and COO—CH$_2$—CH$_2$—, 4H; 1.15 to 1.70 ppm, (m), NCH$_2$CH$_3$, —(CH$_2$)$_7$—, 17H; 0.85 ppm, (t), —(CH$_2$)$_7$—CH$_3$, 3H.

EXAMPLE XI

2-Ethyl Butyl[1-Ethyl 4-Oxo 1,4-Dihydro 7-Methyl 3-Naphthyridinyl]Carboxyloxyacetate (1) 2-ethyl butyl bromoacetate:

101 g (0.5M) of the bromide of bromoacetic acid is run into a solution of 51.1 g (0.5M) of corresponding alcohol, 51.6 g (0.5M) of triethylamine, in 600 ml of anhydrous ether, kept at 10°. It is stirred at ordinary temperature for 15 hours, filtered, the solvent evaporated and distilled under reduced pressure. 57% of a pure product is obtained, b.p.=50° (0.15 mm)

(2) 12.3 g (55 mM) of preceding bromide is added to a suspension of 14.23 g (56 mM) of the sodium salt of [1-ethyl 4-oxo 1,4-dihydro 7-methyl 3-naphthyridinyl]-carboxylic acid in 400 ml of dimethylformamide. It is stirred at ordinary temperature for 48 hours and the solution obtained evaporated to dryness. The residue is taken up again in 150 ml of iced 0.2N caustic soda, and extracted with chloroform. The chloroform layer is washed with 0.5N caustic soda, with water, dried and evaporated. The oily residue is recovered with petroleum ether, then filtered; in this way 90% of a pure product is obtained, Rf=0.45 (A); Rf=0.77 (B); m.p.=82°.

NMR spectrum, in solution in $CDCl_3$, with respect to TMS: 8.70 ppm (s), N=CH, 1 H; 7.25 and 8.55 ppm, (m), H arom, 2H; 4.85 ppm, (s), -COOCH$_2$COO-, 2H; 4.10 and 4.50 ppm, (q) and (d), NCH$_2$CH$_3$ and COO CH$_2$CH-, 4H; 2.65 ppm, (s), =C(CH$_3$)-N, 3H; 1.15 to 1.65 ppm, (m), N-CH$_2$ CH$_3$ and CH(CH$_2$CH$_3$) CH$_2$CH$_3$, 8H; 0.85 ppm, (t), -CH$_2$CH$_3$, 6H.

EXAMPLE XII

2-Ethyl Butyl[1-Ethyl 4-Oxo 6,7-Methylenedioxy 1,4-Dihydro 3-Quinolinyl]Carbonyloxyacetate 12.3 g (55 mM) of the bromide explained in the example XI-1) is added to a suspension of 15.85 g (56 mM) of the sodium salt of [1-ethyl 4-oxo 6,7-methylenedioxy 1,4-dihydro 3-quinolinyl] of carboxylic acid, in 400 ml of dimethylformamide. It is stirred at ordinary temperature for 48 hours and the solution obtained evaporated to dryness. The residue is taken up again in 150 ml of iced 0.2N caustic soda, and extracted with chloroform. The chloroform layer is washed with 0.5N caustic soda, with water, dried and concentrated. The oily residue is recovered by 150 ml of petroleum ether for 15 hours.

After filtration and drying, 93% of a pure product is obtained, Rf=0.2 (A); Rf=0.61 (B); m.p.=102°-4°.

NMR spectrum, in solution in $CDCl_3$, with respect to TMS: 8.35 ppm, (s), N—CH=, 1H; 6.80 and 7.65 ppm, (2s), H arom, 2H; 6.10 ppm, (s), —OCH$_2$O—, 2H; 4.85 ppm, (s), —COOCH$_2$COO—, 2H; 4.05 to 4.35 ppm, (m), N—CH$_2$CH$_3$ and COOCH$_2$CH—, 4H; 1.20 to 1.60 ppm, (m), N—CH$_2$CH$_3$ and CH(CH$_2$CH$_3$)CH$_2$CH$_3$, 8H; 0.75 to 1 ppm, (m), —CH$_2$CH$_3$, 6H.

EXAMPLE XIII

2-Ethyl Hexyl[1-Ethyl 4-Oxo 1,4-Dihydro 7-Methyl 3-Naphtyridinyl]Carbonyloxyacetate (1) 2-ethyl hexyl bromoacetate:

111 g (0.55M) of the bromide of bromoacetic acid is run into a solution of 71.6 g (0.55M) of 2-ethyl hexanol, 56.7 g (0.56M) of triethylamine in 700 ml of anhydrous ether, maintained at 10°. It is stirred at ordinary temperature for 15 hours, filtered, the solvent evaporated and distilled under reduced pressure. 68% of a pure product is obtained, b.p.=65°-7° (0.03 min).

13.8 g (55 mM) of the preceding bromide is added to a suspension of 14.25 g (56 mM) of the sodium salt of [1-ethyl 4-oxo 1,4-dihydro 7-methyl 3-naphtyridinyl] carboxylic acid in 400 ml of dimethylformamide. It is stirred at ordinary temperature for 48 hours and the solution obtained is evaporated to dryness. The residue is taken up again in 150 ml of 0.2N iced caustic soda, extracted with chloroform, the chloroform layer washed with 0.5N caustic soda, with water, dried and evaporated. The residue is covered with petroleum ether. After filtration, drying, 87% of a pure product is obtained, Rf=0.45 (A); Rf=0.80 (B); m.p.=65°-6°.

NMR spectrum, in solution in $CDCl_3$, with respect to TMS: 8.65 ppm, (s), N—CH—, 1H; 7.20 and 8.55 ppm, (m), H arom, 2H; 4.85 ppm, (s), —COOCH$_2$COO—, 2H; 4.10 and 4.50 ppm, (q) and (d), NCH$_2$CH$_3$ and COOCH$_2$CH—, 4H; 2.65 ppm, (s), =C(CH$_3$)—N, 3H; 1.15 to 1.65 ppm, (m), N—CH$_2$CH$_3$ and CH(CH$_2$CH$_3$)CH$_2$CH$_2$CH$_2$CH$_3$, 12H; 0.90 ppm, (t), —CH$_2$CH$_3$, 6H.

EXAMPLE XIV

2-Ethyl Hexyl [1-Ethyl 4-Oxo 6,7-Methylenedioxy 1,4-Dihydro 3-Quinolinyl]Carbonyloxyacetate 13.8 g (55 mM) of the bromide explained in example XIII-1 is added to a suspension of 15.85 g (56 mM) of the sodium salt of [1-ethyl 4-oxo 6,7-methylenedioxy 1,4-dihydro 3-quinolinyl]carboxylic acid in 400 ml of dimethylformamide. It is stirred at ordinary temperature for 48 hours and the solution obtained evaporated to dryness. The residue is taken up again in 150 ml of iced 0.2N caustic soda, extracted with chloroform. The chloroform layer is washed with 0.5N caustic soda, with water, dried, evaporated, the residue covered with petroleum ether for 15 hours. After filtration and drying, 92% of a pure product is obtained, Rf=0.17 (A); Rf=0.60 (B); m.p.=71°-3°.

NMR spectrum, in solution in $CDCl_3$, with respect to TMS: 8.35 ppm, (s); N—CH, 1H; 6.80 and 7.65 ppm, (2s), H arom, 2H; 6.10 ppm, (s), —OCH$_2$O—, 2H; 4.85 ppm, (s), COOCH$_2$COO, 2H; 4 to 4.30 ppm, (m), NCH$_2$CH$_3$ and COOCH$_2$CH—, 4H; 1.05 to 1.60 ppm, (m), N—CH$_2$CH$_3$ and CH(CH$_2$CH$_3$)CH$_2$CH$_2$CH$_2$CH$_3$, 12H; 0.75 to 1 ppm, —CH$_2$CH$_3$, 6 H.

EXAMPLE XV

Cyclohexylmethyl [1-Ethyl 4-Oxo 1,4-Dihydro 7-Methyl 3-Naphtyridinyl]Carbonyloxyacetate (1) Cyclohexylmethyl bromoacetate:

100.9 g (0.5M) of the bromide of bromoacetic acid is run into a solution of 57.1 g (0.5 M) of cyclohexylmethanol, 51.6 g (0.51 M) of triethylamine, in 600 ml of anhydrous ether, at 10°. It is stirred at ordinary temperature for 15 hours, filtered, the solvent evaporated and distilled under reduced pressure. 60% of a pure product is obtained, b.p.=60° C. (0.25 mm)

(2) 12.9 g (55 mM) of the preceding bromide is added to a suspension of 14.23 g (56 mM) of the sodium salt of [1-ethyl 4-oxo 1,4-dihydro 7-methyl 3-naphtyridinyl]-carboxylic acid, in 400 ml of dimethylformamide. It is stirred at ordinary temperature for 48 hours and the solution obtained evaporated to dryness. The residue is taken up again in 150 ml of iced 0.2N caustic soda, extracted with chloroform. The chloroform layer is washed with 0.5N caustci soda, with water, dried, concentrated. The oily residue is covered with petroleum ether. After filtration and drying, 92% of a pure product is obtained, Rf=0.40 (A) Rf=0.73 (B); m.p.=130°-2°.

NMR spectrum, in solution in CDCl$_3$, with respect to TMS: 8.70 ppm, (s) N—CH, 1H; 7.20 and 8.55 ppm (m), H arom, 2H; 4.85 ppm, (s), —COOCH$_2$COO—, 2H; 4.50 ppm, (q), N—CH$_2$CH$_3$, 2H; 4.0 ppm (d), COOCH$_2$-CH—, 2H; 2.65 ppm, (s), =C(CHHD 3)—N, 3H; 1.15 to 1.85 ppm, —NCH$_2$CHHD 3 and —CH$_2$C$_6$H$_{11}$, 14H.

EXAMPLE XVI

Cyclohexylmethyl[1-Ethyl 4-Oxo 6,7-Methyllenedioxy 1,4-Dihydro 3-Quinolinyl]Carbonyloxyacetate 12.9 g (55 mM) of the bromide, explained in example XV-1), is added to a suspension of 15.85 (56 mM) of the sodium salt of [1-ethyl 4-oxo 6,7-methylenedioxy 1,4-dihydro 3-quinolinyl]carboxylic acid, in 400 ml of dimethylformamide.

It is stirred at ordinary temperature for 48 hours and the solution obtained evaporated to dryness. The residue is taken up again in 150 ml of 0.2N iced caustic soda, extracted with chloroform. The chloroform layer is washed with 0.5N caustic soda, with water, dried, evaporated, and the residue covered with petroleum ether.

After filtration and drying, 92% of a pure product is obtained, Rf=0.23 (A); Rf=0.61 (B); m.p.=119°-20°.

NMR spectrum, in solution in CDCl$_3$, with respect to TMS: 8.35 ppm, (s), N—CH, 1H; 6.80 and 7.65 ppm, (2s), H arom, 2H; 6.10 ppm, (s), —OCH$_2$O—, 2H; 4.85 ppm, (s), COOCH$_2$COO—, 2H; 3.95 to 4.30 ppm, (m), N—CH$_2$CH$_3$ and COOCH$_2$CH—, 4H; 0.90 to 1.85 ppm, NCH$_2$CH$_3$ and CH$_2$—C$_6$H$_{11}$, 14H.

EXAMPLE XVII

Ter-Butyl[1-Ethyl 4-Oxo 1,4 Dihydro 7-Methyl 3-Naphtyridinyl]carbonyloxyacetate 13.5 g (69 mM) of t.butyl 2-bromoacetate is added to a suspension of 17.8 g (70 mM) of the sodium salt of [1-ethyl 4-oxo 1,4-dihydro 7-methyl 3-naphtyridinyl]-carboxylic acid, suspended in 500 ml of dimethylformamide. It is stirred at ordinary temperature for 48 hours, and the solution obtained is evaporated to dryness. The residue is taken up again in water, extracted with chloroform, the chloroform layer washed with 0.5N iced caustic soda, and water. After drying, it is evaporated and taken up for several hours in petroleum ether. It is filtered, dried and 88% of a pure product is obtained, Rf=0.79 (B); Rf=0.85 (C); m.p.=151°-2°.

NMR spectrum, in solution in CDCl$_3$, with respect to TMS: 8.70 ppm, (s), N=CH, 1H; 7.25 and 8.55 ppm, (m), H arom, 2H; 4.75 ppm, (s), —COOCH$_2$Coo—, 2 2H; 4.45 ppm, (q), NCH$_2$CH$_3$, 2H; 2.65 ppm, (s)=C(CH$_3$)—N—, 3H; 1.45 to 1.65 ppm, (s) and (t), NCH$_2$CH$_3$ and —C(CH$_3$)$_3$, 12H.

EXAMPLE XVIII

Ter-Butyl[1-Ethyl 4-Oxo 6,7 Methylenedioxy 1,4-Dihydro 3-Quinolinyl]Carbonyloxy Acetate 13.4 g (69 mM) of t-butyl bromoacetate is run into a suspension of 19.8 g (70 mM) of the sodium salt of [1-ethyl 4-oxo 6,7-methylenedioxy 1,4-dihydro 3-quinolinyl]carboxylic acid, in 500 ml of dimethylformamide. It is stirred at ordinary temperature for 48 hours, and the solution obtained evaporated to dryness. The residue is taken up again with 200 ml of iced water, and extracted with chloroform. The chloroform layer is washed with 0.5N caustic soda, with water, dried and evaporated. The oily residue crystallizes hot in petroleum ether. After filtration, drying, 91% of a pure product is obtained, Rf=0.11 (A); Rf=0.59 (B); m.p.=176°.

NMR spectrum, in solution in CDCl$_3$, with respect to TMS: 8.35 ppm, (s), —N—CH=, 1H; 6.80 and 7.65 ppm, (2s), H arom, 2H; 6.10 ppm, (s), —O—CHHD 2—O—, 2H 4.70 ppm, (s), —COO—CH$_2$—COO—, 2H; 4.15 ppm, (q), NCH$_2$CH$_3$, 2H; 1.45 ppm, (s), —C(CH$_3$)$_3$, 9H; 1.15 to 1.35 ppm, (t), N—CH$_2$CH$_3$, 3H.

EXAMPLE XIX

Benzyl[1-Ethyl 4-Oxo 6,7-Methylenedioxy 1,4-Dihydro 3-Quinolinyl]carbonyloxyacetate 14 g (61 mM) of benzyl 2-bromoacetate is run into a suspension of 17 g (60 mM) of the sodium salt of [1-ethyl 4-oxo 6,7-methylenedioxy 1,4 dihydro 3-quinolinyl]carboxylic acid, in 400 ml of dimethylformamide. It is stirred at ordinary temperature for 48 hours and evaporated to dryness. The residue is taken up again with 200 ml of 0.2N cold caustic soda, and extracted with chloroform. The chloroform layer is washed with 0.5N caustic soda, with water, dried and evaporated to dryness. The solid residue is made into a paste in 300 ml of petroleum ether. It is filtered, dried and 91% of a pure product obtained, Rf=0.78 (B), Rf=0.64 (C), m.p.=152°-3°.

NMR spectrum, in solution in CDCl$_3$, with respect to TMS: 8.35 ppm, (s), N—CH=, 1H; 6.80 and 7.70 ppm, (2s), H arom, 2H; 7.35 ppm, (s), CH$_2$—C$_6$H$_5$, 5H; 6.05 ppm, (s), —O—CH$_2$—O, 2H; 5.20 ppm, (s), CH$_2$—C$_6$H$_5$, 2H; 4.90 ppm, (s), —COO—CH$_2$—COO—, 2H; 4.10 ppm, (q), N—CH$_2$CH$_3$, 2H; 1.50 ppm, (t), NCH$_2$CH$_3$, 3H.

EXAMPLE XX

T-Butyl[1-Ethyl 4-Oxo 6,7-Methylenedioxy 1,4-Dihydro 3-Quinolinyl]6-Carbonyloxy Hexanoate (1) t-butyl 6-bromo, hexanoate:

1.2 ml of concentrated sulfuric acid, is run drop by drop, on to a mixture of 48.8 g (0.25M) of 6-bromo hexanoic acid and 5 ml of t-butyl alcohol. The mixture is brought to a temperature of 0° and run rapidly to 50.5 g (0.9M) of isobutylene previously liquified in the freezer. It is hermetically sealed and then stirred for 15 hours at ordinary temperature. The solution obtained is cooled, treated with a saturated solution of sodium bicarbonate to a pH in the vicinity of 7–8. It is extracted with ether, washed with iced water, dried and distilled; 81% of a pure product is obtained, b.p.=126–8° (13 mm), Rf=0.81 (CHCl$_3$).

(2) 12.6 g (50 mM) of t-butyl 6-bromo hexanoate is run on to a suspension of 14.5 g (51 (51 mM) of the sodium salt of [1-ethyl 4-oxo 6,7-methylenedioxy 1,4-dihydro 3-quinolinyl]carboxylic acid in 400 ml of dimethylformamide. It is stirred at ordinary temperature for 48 hours, the solution evaporated to dryness, the residue taken up again in 150 150 ml of iced water, extracted with chloroform. The chloroform layer is washed with 0.5N caustic soda, with water, dried and evaporated. The oily residue is made into a paste with petroleum ether, in the cold, for some hours. It is filtered, dried and 23% of a pure product is obtained, Rf=0.69 (B), Rf=0.62 (C), m.p.=81°–3°.

NMR spectrum in solution in d$_6$ dimethylsulfoxide, with respect to TMS: 8.60 ppm, (s), —N—C$\underline{H}$=, 1H; 7.45 and 7.60 ppm, (2 s), H arom, 2H; 6.30 ppm, (s), —OC$\underline{H_2}$O—, 2H; 4.25 and 4.45 ppm, (m), NC$\underline{H_2}$CH$_3$ and COOC$\underline{H_2}$—(CH$_2$)$_4$—4H; 2.30 ppm, (t), —(CH$_2$)$_4$C$\underline{H_2}$COO—, 2H; 1.50 to 1.70 ppm (m), COOCH$_2$(C$\underline{H_2}$)$_3$CH$_2$, 6H; 1.20 and 1.45 ppm, (t) and (s), —NCH$_2$C$\underline{H_3}$, C(C$\underline{H_3}$)$_3$, 12H.

EXAMPLE XXI

[1-Ethyl 4-Oxo 1,4-Dihydro 7-Methyl 3-Naphtyridinyl]Carbonyloxyacetic Acid 13.85 g (40 mM) of the corresponding t-butyl acetate, prepared according to example XVII, is added in one lot to a solution of 140 ml trifluoroacetic acid, previously kept at 0°. It is stirred for 30 minutes in the cold, then for 2 hours at ordinary temperature. It is evaporated to dryness and diluted with ethyl ether. It is stirred in the cold for 30 minutes, filtered and dried. 96% of a pure product is obtained, Rf=0.05 (A) Rf=0.23 (C), m.p.=219°–21°.

NMR spectrum, in solution in CDCl$_3$, with respect to TMS: 8.70 ppm, (s), —N—CH=, 1H; 7.30 and 8.55 ppm, (m), H arom, 2H; 6.60 ppm, (m) —COOH, H interchangeable with water, 1H 4.95 ppm, (s), COOC$\underline{H}$ $_2$COO, 2H; 4.55 ppm (q), NC$\underline{H_2}$CH$_3$, 2H; 2.70 ppm, (s), =C(C$\underline{H_3}$)—N—, 3H; 1.50 ppm, (t), NCH$_2$C$\underline{H_3}$, 3H.

EXAMPLE XXII

[1-Ethyl 4-Oxo 6,7-Methylenedioxy 1,4-Dihydro 3-Quinolinyl]Carbonyloxy Acetic Acid At ordinary temperature and atmospheric pressure 18.4 g (45 mM) of the corresponding benzyl ester (explained in example XIX), in 300 ml of acetic acid, is hydrogenated in the presence of 2 g of 5% palladium on C. After filtration of the catalyst, at 80°, it is evaporated to dryness and the residue taken up again with ethyl ether. It is filtered, dried and the solid residue taken up with iced water, neutralised with 2N of caustic soda and reprecipitated with concentrated hydrochloric acid in the cold. 92% of a pure product is obtained, Rf=0.12 (C), m.p.=240°–3°.

NMR spectrum, in solution in NaOD 0.5N: 8.60 ppm, (s), —N—C$\underline{H}$=, 1H; 6.95 and 7.30 ppm, (m), H arom, 2H; 6.25 ppm (s), OC$\underline{H_2}$O, 2H; 4.90 ppm, (s), —COOC$\underline{H}$ $_2$COO—, 2H; 4.25 ppm, (m), NC$\underline{H_2}$CH$_3$, 2H; 1.50 ppm, (m), NCH$_2$C$\underline{H_3}$, 3H.

EXAMPLE XXIII

[1-Ethyl 4-Oxo 6,7-Methylenedioxy 1,4-Dihydro 3-Quinolinyl]6-Carbonyloxy Hexanoic Acid 3.9 g (9 mM) of the corresponding t-butyl ester (prepared according to example XX), is added to a solution of 25 ml of trifluoroacetic acid, previously maintained at 0°. It is stirred for 30 minutes in the cold, 90 minutes at ordinary temperature, evaporated to dryness and covered with 200 ml of ethyl ether. It is stirred for 30 minutes in the cold, filtered and dried. 90% of a pure product is obtained, Rf=0.55 (C) m.p. =207°–9°.

EXAMPLE XXIV

Benzyl[1-Ethyl 4-Oxo 6,7-Methylenedioxy 1,4-Dihydro 3-Quinolinyl]2-Carbonyloxy Propionate 34 g (0.14M) of benzyl 2-bromo propionate, prepared according to the procedure described in example XI-1), is run into a suspension of 39.6 g (0.14M) of the sodium salt of [1-ethyl 4-oxo 6,7-methylenedioxy 1,4-dihydro 3-quinolinyl]carboxylic acid in 900 ml of dimethylformamide. There is obtained, according to the technique explained for ethyl 2-bromo butyrate (example IV), 73% of a pure product, Rf=0.16 (A); Rf=0.85 (B); m.p.=129°–30°.

NMR spectrum, in solution in CDCl$_3$, with respect to TMS: 8.30 ppm, (s), —N—C$\underline{H}$=; 1H; 6.80 and 7.60 ppm, (2 s), H arom, 2H; 7.30 ppm, (s), C$\underline{H_2}$C$_6$H$_5$, 5H; 6.05 ppm, (s), —OC$\underline{H_2}$O—, 2H; 5.15 to 5.45 ppm, (q), —C$\underline{H}$(CH$_3$)—, 1H; 5.20 ppm, (s), —C$\underline{H_2}$C$_6$H$_5$, 2H; 4.10 ppm, (q); NC$\underline{H_2}$CH$_3$, 2H; 1.65 ppm, (d), —CH(C$\underline{H_3}$)—, 3H; 1.35 ppm (t), NCH$_2$C$\underline{H_3}$, 3H.

EXAMPLE XXV

Benzyl[1-Ethyl 4-Oxo 6,7-Methylenedioxy 1,4-Dihydro 3-Quinolinyl]2-Carbonyloxy Butyrate 34.7 g (0.135M) of benzyl 2-bromo butyrate, (prepared according to the example XI-1) is run into a suspension of 38.2 g (0.135M) of the sodium salt of [1-ethyl 4-oxo 6,7-methylenedioxy, 1,4-dihydro 3-quinolinyl]carboxylic acid, in 900 ml of dimethylformamide. There is obtained, according to the technique described in example IV, 40% of a pure product, Rf=0.10 (A); Rf=0.60 (B); m.p.=129°–31°.

NMR spectrum, in solution in CDCl$_3$, with respect to TMS: 8.50 ppm, (s); —N—C$\underline{H}$=, 1H; 7.15 and 7.60 ppm, (2 s), H arom, 2H; 7.30 ppm, (s), C$\underline{H_2}$C$_6$H$_5$, 5H; 6.10 ppm, (s), —OC$\underline{H_2}$O—, 2H; 5 to 5.20 ppm, (s) and solid C$\underline{H}$(C$_2$H$_5$)— and C$\underline{H_2}$C$_6$H$_5$, 3H; 4.10 to 4.45 ppm, (q), NC$\underline{H_2}$CH$_3$, 2H; 1.95 ppm, (m), —CH(C$\underline{H_2}$CH$_3$)—, 2H; 1.40 ppm, (t), NCH$_2$C$\underline{H_3}$, 3H; 1.05 ppm, (t), —CH(CH$_2$C$\underline{H_3}$), 3H.

EXAMPLE XXVI

Benzyl[1-Ethyl 4-Oxo 6,7-Methylenedioxy 1,4-Dihydro 3-Quinolinyl]2Carbonyloxy Hexanoate 31.4 g (0.11M) of benzyl 2-bromo hexanoate, prepared according example XI-1), is run into a suspension of 31.2 g (0.11M) of the sodium salt of [1-ethyl 4-oxo 6,7-methylenedioxy 1,4-dihydro 3-quinolinyl]carboxyli acid, in 750 ml of dimethylformamide. There is obtained, according to the technique described in example IV, 48% of a pure product; Rf=0.21 (A); Rf=0.71 (C); m.p.=93°.

NMR spectrum, in solution in CDCl$_3$, with respect to TMS: 8.30 ppm, (s), —N—C$\underline{H}$=, 1H; 6.90 and 7.70 ppm, (2s), H arom, 2H; 7.35 ppm, (s), —CH$_2$C$_6$H$_5$, 5H; 6.05 ppm, (s), —OC$\underline{H}_2$O—, 2H; 5.10 to 5.40 ppm, (s) and solid —C$\underline{H}$(C$_4$H$_9$)— and C$\underline{H}_2$C$_6$H$_5$, 3H; 3.95 to 4.30 ppm, (q), NC$\underline{H}_2$CH$_3$, 2H; 1.40 ppm, (t), NCH$_2$C$\underline{H}_3$, 3H; 0.90 to 2.05 ppm, (m), —CH(C$_4$H$_9$)—, 9H.

EXAMPLE XXVII

Benzyl[1-Ethyl 4-Oxo 6,7-Methylenedioxy 1,4-Dihydro 3-Quinolinyl]2-carbonyloxy 2-Phenyl Acetate 36.6 g (0.11M) of benzyl bromo phenylacetate, prepared according to example XI-1, is run into a suspension of 31.2 g (0.11M) of the sodium salt of [1-ethyl 4-oxo 6,7-methylenedioxy 1,4-dihydro 3-quinolinyl]carboxylic acid in 750 ml of dimethylformamide.

There is obtained, according to the technique described in example IV, 89% of a pure product, Rf=0.27 (A); Rf=0.82 (C), m.p.=133°-5°.

NMR spectrum, in solution in CDCl$_3$, with respect to TMS: 8.50 ppm, (s), N—C$\underline{H}$=, 1H; 6.95 to 7.65 ppm, (m), H arom, 12H; 6.10 ppm, (2s), —OCH$_2$O— and —C$\underline{H}$(C$_6$H$_5$)—, 3H; 5.10 ppm, (s), —C$\underline{H}_2$C$_6$H$_5$, 2H; 4.05 to 4.30 ppm, (q), NC$\underline{H}_2$CH$_3$, 2H; 1.35 ppm, (t), —NCH$_2$C$\underline{H}_3$, 3H.

EXAMPLE XXVIII

[1-Ethyl 4-Oxo 6,7-Methylenedioxy 1,4-Dihydro 3-Quinolinyl]2-Carbonyloxy Propionic Acid From the corresponding benzyl ester (example XXIV), there is obtained by catalytic hydrogenation according to the technique described in example XXII, 85% of a pure product, Rf=0.06 (B), Rf=0.12 (C), m.p.=219°-21°.

EXAMPLE XXIX

[1-Ethyl 4-Oxo 6,7-Methylenedioxy 1,4-Dihydro 3-Quinolinyl]2-Carbonyloxy Butyric Acid From the corresponding benzyl ester (example XXV), there is obtained, by catalytic hydrogenation, according to the technique described in example XXII, 90% of a pure product, Rf=0.08 (B), Rf=0.21 (C); m.p.=214°-7°.

EXAMPLE XXX

[1-Ethyl 4-Oxo 6,7-Methylenedioxy 1,4-Dihydro 3-Quinolinyl]2-Carbonyloxy Hexanoic Acid From the corresponding benzyl ester (example XXVI), there is obtained by catalytic hydrogenation by the technique described in example XXII, 91% of a pure product, Rf=0.12 (B), Rf=0.40 (C), m.p.=131°-4°.

The antibacterial agents according to the invention possess in addition interesting pharmacological properties. They are revealed to be diuretics, muscle relaxants, bronchodilators and anti-depression agents.

Thus, in bronchospasm provoked by aceylcholine in the animal, the bronchodilator activities are comparable even superior to those of theophylline. Bronchospasms induced in the isolated trachea of the guinea pig are antagonized by the derivatives according to the invention and propanolol does not reduce this relaxant effect indicating the possible absence of $\beta_2$ agonist action.

The derivatives according to the invention antagonize various agonists: histamine, acetylcholine, serotonin and baryum chloride at concentrations reaching 2–10$^{-7}$ Mole/ml. They inhibit inotropic activity induced by histamine.

At 30 mg/kg, they are revealed to be anti-depressant agents in the mouse/according to Vermier—First Hahnemann—Symposium on Psychosomatic Medecines ed. Nodine and Mayer p. 683-1962. At the same doses, the majority of the products according to the invention show diuretic activity in the rat.

Applicants have also observed that these compounds posses remarkable anti-bacterial activities with respect, particularly, to gram. negative bacteria and groups of bacteria resistant to known chemotherapeutic agents.

The compounds according to the invention may be used as medicaments in the form of the usual pharmaceutical preparations. The latter may be administered orally, parenterally, rectally, transdermally or in the form of aerosols alone or with excipients adapted to each galenic form.

The posology of administration of the compounds according to the invention varies according to the route of administration, the age, the weight and the condition of the patients and the particular disease to be treated. In general, it is possible to use these active principles at daily doses of 1 to 50 mg/kg and in particular from 2 to 20 mg/kg.

We claim:

1. A compound according to the formula:

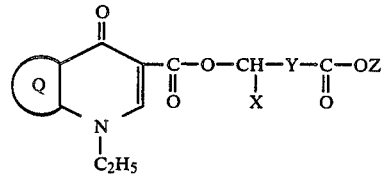

and their addition salts formed from pharmaceutically acceptable acids and bases, in which:

Q is selected from the class consisting of aromatic rings optionally substituted by fluoro, piperazinyl, pyridinyl, methyl or methylenedioxy and six member heterocyclic rings optionally substituted by flouro, piperazinyl, pyridinyl, methyl or mehtylenedioxy having 1 to 2 nitrogen atoms, wherein at least one of said nitrogen atoms is in an ortho position with regard to the condensed linkage between pyridone and the heterocyclic ring and defines with the pyridone ring the class consisting of optionally substituted quinolines, optionally substituted naphthyridines and optionally substituted piromidic derivatives;

Z is selected from the class consisting of (a) hydrogen, (b) linear or branched alkyl groups comprising from 1 to 9 carbon atoms, (c) cyclohexylmethyl, and (d) benzyl;

X is selected from the class consisting of hydrogen, linear or branched alkyl groups having from 1 to 6 carbon atoms, and phenyl; and Y is a direct linkage or is a linear or branched alkylene group having from 1 to 10 carbon atoms.

2. The derivatives according to claim 1 wherein Q determines with the pyridone group the derivative 1-ethyl 1,4-dihydro 6,7-methylenedioxy 4-oxo 3-quinolyl.

3. The derivatives according to claim 1 wherein Q determines with the pyridone group the derivative 1-ethyl 1,4-dihydro 7-methyl 4-oxo 3-naphtyridinyl.

4. Derivative according to claim 1 constituted by ethyl[1-ethyl 1,4-dihydro 7-methyl 4-oxo 3-naphtyridinyl]4-carbonyloxy butyrate.

5. Derivative according to claim 1 which is constituted by ethyl[1-ethyl 4-oxo 6,7-methylenedioxy 1,4-dihydro 3-quinolinyl]4-carbonyloxy butyrate.

6. Derivative according to claim 1 constituted by n-nonyl[1-ethyl 1,4-dihydro 7-methyl 4-oxo 3-naphtyridinyl]carbonyloxy acetate.

7. Derivative according to claim 1 constituted by n-nonyl[1-ethyl 4-oxo 6,7-methylenedioxy 1,4-dihydro 3-quinolinyl]carbonyloxy acetate.

8. An antibacterial agent consisting essentially of a compound in an amount effective to control a bacterial infection in a human or animal subject in a pure state or in association with one or several pharmaceutically acceptable adjuvants or diluents, said compound comprising a compound according to the formula:

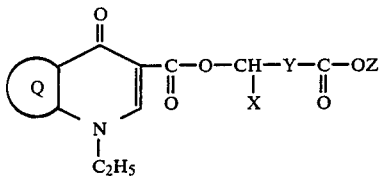

and their addition salts formed from pharmaceutically acceptable acids and bases, in which:

Q is selected from the class consisting of aromatic rings optionally substituted by flouro, piperazinyl, pyridinyl, methyl or mehtylenedioxy, and heterocylic rings optionally substituted by flouro, piperazinyl, pyridinyl, methyl or mehtylenedioxy having from 1 to 2 nitrogen atoms;

Z is selected from the class consisting of (a) hydrogen, (b) linear or branched alkyl groups having from 1 to 9 carbon atoms, (c) cyclohexylmethyl, and (d) benzyl;

X is selected from the class consisting of hydrogen, linear or branched alkyl groups having from 1 to 6 carbon atoms, and phenyl; and Y is a direct linkage or is a linear or branched alkylene group having from 1 to 10 carbon atoms.

9. A method for controlling a bacterial infection in a human or animal subject comprising administering to said subject a compound in an amount effective to control said bacterial infection, said compound comprising a compound according to the formula:

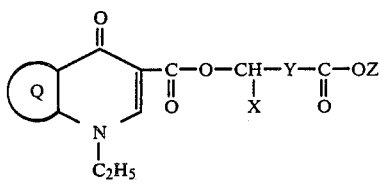

and their addition salts formed from pharmaceutically acceptable acids and bases, in which:

Q is selected from the class consisting of aromatic rings optionally substituted by flouro, piperazinyl, pyridinyl, methyl or methylenedioxy, and heterocyclic rings optionally substituted by flouro, piperazinyl, pyridinyl, methyl or methylenedioxy having from 1 to 2 nitrogen atoms;

Z is selected from the class consisting of (a) hydrogen, (b) linear or branched alkyl groups having from 1 to 9 carbon atoms, (c) cyclohexylmethyl, and (d) benzyl;

X is selected from the class consisting of hydrogen, linear or branched alkyl groups having from 1 to 6 carbon atoms, and phenyl; and Y is a direct linkage or is a linear or branched alkylene group having from 1 to 10 carbon atoms.

* * * * *

UNITED STATES PATENT AND TRADEMARK OFFICE
CERTIFICATE OF CORRECTION

PATENT NO. : 4,764,518

DATED : August 16, 1988

INVENTOR(S) : Claude Laruelle et al.

It is certified that error appears in the above-identified patent and that said Letters Patent is hereby corrected as shown below:

In the Abstract:

Line 10, after the word "group" please change the comma (,) to a period (.).

In the Specification:

Column 2, line 13, in formula (IV), "$R_2R_2N$" should be -- $R_1R_2N$ --.

Column 3, line 61, "3-naphtyridinyl" should be -- 3-naphthyridinyl --.

Column 4, line 37, "tert-butyl" should be -- ter-butyl --.

Column 5, line 33, "3-naphtyridinyl" should be -- 3-naphthyridinyl --.

Column 5, line 67, "acid" should be -- iced --.

Column 6, line 23, "3-naphtyridinyl" should be -- 3-naphthyridinyl --.

Column 6, line 51, please insert -- ] -- after the word "quinolinyl".

Column 6, line 55, "sode" should be -- soda --.

Column 7, line 3, "3-Naphtyridinyl" should be -- 3-Naphthyridinyl --.

UNITED STATES PATENT AND TRADEMARK OFFICE
CERTIFICATE OF CORRECTION

PATENT NO. : 4,764,518

DATED : August 16, 1988

INVENTOR(S) : Claude Laruelle et al.

It is certified that error appears in the above-identified patent and that said Letters Patent is hereby corrected as shown below:

Column 7, line 7, "3-naphtyridinyl" should be
-- 3-naphthyridinyl --.

Column 7, line 51, "3-Naphtyridinyl" should be
-- 3-Naphthyridinyl --.

Column 7, line 62, "3naphtyridinyl" should be
-- 3-naphthyridinyl --.

Column 7, line 66, "exstracted" should be -- extracted --.

Column 8, line 52, "3-naphtyridinyl" should be
-- 3-naphthyridinyl --.

Column 9, line 41, "3-naphtyridinyl" should be
-- 3-naphthyridinyl --.

Column 9, line 53, "N=CH" should be -- N=C$\underline{H}$ --.

Column 9, line 54, "-COOCH$_2$COO-" should be -- -COOC$\underline{H}_2$COO- --.

Column 9, line 55, "NCH$_2$CH$_3$" should be -- NC$\underline{H}_2$CH$_3$ --.

Column 9, line 56, "CH$_2$CH-" should be -- $\underline{CH}_2$CH- --.

Column 9, line 56, "=C(CH$_3$)-N" should be -- =C($\underline{CH}_3$)-N --.

Column 9, line 57, "CH$_3$" should be -- $\underline{CH}_3$ --.

Column 9, line 57, "CH(CH$_2$CH$_3$)" should be -- $\underline{CH}$($\underline{CH}_2$CH$_3$) --.

UNITED STATES PATENT AND TRADEMARK OFFICE
CERTIFICATE OF CORRECTION

PATENT NO. : 4,764,518

DATED : August 16, 1988

INVENTOR(S) : Claude Laruelle et al.

It is certified that error appears in the above-identified patent and that said Letters Patent is hereby corrected as shown below:

Column 9, line 58, "CH$_2$CH$_3$" should be -- $\underline{CH}_2CH_3$ --.

Column 9, line 58, "-CH$_2$CH$_3$" should be -- -CH$_2\underline{CH}_3$ --.

Column 10, line 20, "3-Naphtyridinyl" should be -- 3-Naphthyridinyl --.

Column 10, line 32, "3-naphtyridinyl" should be -- 3-naphthyridinyl --.

Column 11, line 9, "3-Naphtyridinyl" should be -- 3-Naphthyridinyl --.

Column 11, line 20, "3-naphtyridinyl" should be -- 3-naphthyridinyl --.

Column 11, line 26, "caustci" should be -- caustic --.

Column 11, line 35, "=C($\underline{C}$HHD 3)-N" should be -- =C($\underline{CH}_3$)-N --.

Column 11, line 36, "-NCH$_2\underline{C}$HHD 3" should be -- -N CH$_2$ $\underline{CH}_3$ --.

Column 11, line 39, "6,7-Methyllenedioxy" should be -- 6,7-Methylenedioxy --.

Column 11, line 64, "3-Naphtyridinyl" should be -- 3-Naphthyridinyl --.

Column 11, line 67, "3-naphtyridinyl" should be -- 3-naphthyridinyl --.

UNITED STATES PATENT AND TRADEMARK OFFICE
CERTIFICATE OF CORRECTION

PATENT NO. : 4,764,518

DATED : August 16, 1988

INVENTOR(S) : Claude Laruelle et al.

It is certified that error appears in the above-identified patent and that said Letters Patent is hereby corrected as shown below:

Column 12, lines 35 and 36, "-O-CHHD 2-O-" should be
-- -O-$\underline{CH}_2$-O- --.

Column 12, line 37, "-C(CH$_3$)$_3$" should be -- -C($\underline{CH}_3$)$_3$ --.

Column 13, line 19, please delete the second occurrence of "150".

Column 13, line 37, "3-Naphtyridinyl" should be
-- 3-Naphthyridinyl --.

Column 13, line 65, "neutralised" should be -- neutralized --.

Column 14, line 62, "2Carbonyloxy" should be
-- 2-Carbonyloxy --.

Column 14, line 65, please insert the word -- to -- after the word "according" and before the word "example".

In the Claims:

Column 16, line 47, "flouro" should be -- fluoro --.

Column 16, lines 47 and 48, "mehtylenedioxy" should be
-- methylenedioxy --.

Column 17, line 3, "3-naphtyridinyl" should be
-- 3-naphthyridinyl --.

UNITED STATES PATENT AND TRADEMARK OFFICE
CERTIFICATE OF CORRECTION

PATENT NO. : 4,764,518

DATED : August 16, 1988

INVENTOR(S) : Claude Laruelle et al.

It is certified that error appears in the above-identified patent and that said Letters Patent is hereby corrected as shown below:

Column 17, lines 5 and 6, "3-naphtyridinyl" should be
-- 3-naphthyridinyl --.

Column 17, lines 11 and 12, "3-naphtyridinyl" should be
-- 3-naphthyridinyl --.

Column 17, line 34, "flouro" should be -- fluoro --.

Column 17, line 35, "mehtylenedioxy" should be
-- methylenedioxy --.

Column 17, lines 35 and 36 "heterocylic" should be
-- heterocyclic --.

Column 17, line 36, "flouro" should be -- fluoro --.

Column 17, line 37, "mehtylenedioxy" should be
-- methylenedioxy --.

Column 18, line 26, "flouro" should be -- fluoro --.

Column 18, line 28, "flouro" should be -- fluoro --.

Signed and Sealed this

Eighteenth Day of April, 1989

Attest:

DONALD J. QUIGG

*Attesting Officer*    *Commissioner of Patents and Trademarks*